(12) United States Patent
Angulo (10) Patent No.: US 10,898,750 B1
(45) Date of Patent: Jan. 26, 2021

(54) BODY ALIGNMENT AND CORRECTION DEVICE

(71) Applicant: Cindy F. Angulo, Fountain Hills, AZ (US)

(72) Inventor: Cindy F. Angulo, Fountain Hills, AZ (US)

(73) Assignee: CFA Enterprises LLC, Fountain Hills, AZ (US)

( * ) Notice: Subject to any disclaimer, the term of this patent is extended or adjusted under 35 U.S.C. 154(b) by 0 days.

(21) Appl. No.: 16/520,987

(22) Filed: Jul. 24, 2019

Related U.S. Application Data (63) Continuation of application No. 15/075,072, filed on Mar. 18, 2016, now abandoned, which is a
(Continued)

(51) Int. Cl.
| | | |
|---|---|---|
| *A63B 21/055* | (2006.01) | |
| *A61F 5/02* | (2006.01) | |
| *A63B 21/068* | (2006.01) | |
| *A63B 69/00* | (2006.01) | |
| *A63B 21/00* | (2006.01) | |
| *A63B 23/02* | (2006.01) | |
| *A63B 71/02* | (2006.01) | |
| *A61F 5/30* | (2006.01) | |
| *A63B 21/16* | (2006.01) | |
| *A63B 21/072* | (2006.01) | |

(Continued)

(52) U.S. Cl.
CPC .......... *A63B 21/0552* (2013.01); *A61F 5/028* (2013.01); *A61F 5/30* (2013.01); *A63B 21/068* (2013.01); *A63B 21/16* (2013.01); *A63B 21/4009* (2015.10); *A63B 23/0233* (2013.01); *A63B 69/0057* (2013.01); *A63B 71/023* (2013.01); *A63B 21/00061* (2013.01); *A63B 21/00065* (2013.01); *A63B 21/0724* (2013.01); *A63B 21/4035* (2015.10); *A63B 23/0205* (2013.01); *A63B 23/03525* (2013.01); *A63B 23/03541* (2013.01); *A63B 2022/0094* (2013.01); *A63B 2209/10* (2013.01); *A63B 2210/50* (2013.01); *A63B 2225/09* (2013.01)

(58) Field of Classification Search
CPC ............ A63B 21/0552; A63B 21/4009; A63B 71/023; A63B 21/0557; A63B 69/0057; A63B 21/16; A63B 21/00061; A63B 2023/003; A63B 23/047; A63B 23/03541; A63B 23/03525
See application file for complete search history.

(56) References Cited

U.S. PATENT DOCUMENTS

| | | | | |
|---|---|---|---|---|
| 1,402,179 | A | * | 1/1922 | Piscitelli ............ A63B 21/0004 482/124 |
| 1,940,904 | A | * | 12/1933 | Dayton .................... A61F 5/03 602/19 |

(Continued)

*Primary Examiner* — Garrett K Atkinson
(74) *Attorney, Agent, or Firm* — R. Randall Frisk (57) ABSTRACT

The body alignment and correction device disclosed herein includes a belt for wearing about the waist of a user. The device further includes removable and repositionable foam blocks to displace portions of the belt away from the user's body. A method of stimulating abdominal or back muscles of a user of the device by selectively placing foam blocks to space a portion of the belt away from a user's body is also disclosed.

18 Claims, 7 Drawing Sheets

Related U.S. Application Data continuation-in-part of application No. 14/987,148, filed on Jan. 4, 2016, now abandoned.

(60) Provisional application No. 62/099,606, filed on Jan. 5, 2015.

(51) Int. Cl.
  *A63B 23/035* (2006.01)
  *A63B 22/00* (2006.01)

(56) References Cited

U.S. PATENT DOCUMENTS

| | | | | |
|---|---|---|---|---|
| 2,574,178 A * | 11/1951 | Haller | A62B 35/0031 | 182/3 |
| 3,532,340 A * | 10/1970 | Nardiello | A63B 19/00 | 482/124 |
| 4,178,923 A * | 12/1979 | Curlee | A61F 5/34 | 128/DIG. 20 |
| 4,492,236 A * | 1/1985 | Pile | A61B 5/107 | 33/515 |
| 4,527,289 A * | 7/1985 | Shea | A41F 9/002 | 2/322 |
| 4,616,639 A * | 10/1986 | Huber | A61F 5/01 | 128/99.1 |
| 4,627,109 A * | 12/1986 | Carabelli | A61F 5/028 | 2/300 |
| 4,984,786 A * | 1/1991 | Lemke | A63B 21/4001 | 482/105 |
| 5,035,523 A * | 7/1991 | Allinder | A41F 9/002 | 15/104.94 |
| 5,147,261 A * | 9/1992 | Smith | A61F 5/028 | 2/338 |
| 5,403,253 A * | 4/1995 | Gaylord | A63B 21/068 | 482/140 |
| 5,411,461 A * | 5/1995 | Thomascik | A63C 3/00 | 280/1.5 |
| 5,620,234 A * | 4/1997 | Gunby | B60R 22/00 | 297/482 |
| 5,688,212 A * | 11/1997 | Walker | A63B 69/0057 | 473/215 |
| 5,984,797 A * | 11/1999 | Kessler | A63B 69/3608 | 473/216 |
| 5,984,836 A * | 11/1999 | Casali | A63B 21/0552 | 482/10 |
| 6,026,531 A * | 2/2000 | Pruitt | A47K 7/022 | 15/160 |
| 6,050,364 A * | 4/2000 | Popall | A62B 35/0031 | 182/6 |
| 6,273,467 B1 * | 8/2001 | Berke | B60R 22/14 | 280/751 |
| 6,350,249 B1 * | 2/2002 | Zicherman | A61H 23/0254 | 601/49 |
| 6,431,991 B1 * | 8/2002 | Kossnar | A63B 69/3608 | 473/216 |
| 6,551,196 B1 * | 4/2003 | Kossnar | A63B 69/3608 | 473/216 |
| 6,645,128 B1 * | 11/2003 | Hur | A63B 21/0004 | 482/105 |
| 6,711,750 B1 * | 3/2004 | Yoo | A61F 7/02 | 2/338 |
| 6,814,645 B2 * | 11/2004 | Kuk | A63B 19/00 | 446/236 |
| 7,410,318 B2 * | 8/2008 | Chambers | A45D 34/04 | 15/104.94 |
| 7,575,136 B2 * | 8/2009 | Kernkamp | A45F 3/14 | 224/158 |
| 7,758,480 B1 * | 7/2010 | Chen | A63B 19/00 | 482/105 |
| 7,914,473 B2 * | 3/2011 | Josey | A63B 23/0244 | 600/594 |
| 8,088,045 B2 * | 1/2012 | Hoffman | A63B 21/055 | 482/1 |
| 8,192,336 B2 * | 6/2012 | Jacob | A63B 21/4009 | 482/121 |
| 9,005,090 B2 * | 4/2015 | Latronica | A63B 23/0238 | 482/139 |
| 9,302,150 B2 * | 4/2016 | Tsuzuki | A63B 21/023 | |
| 9,555,283 B2 * | 1/2017 | Jolly | A63B 23/025 | |
| 9,687,688 B2 * | 6/2017 | Hsiao | A63B 19/00 | |
| 2003/0027698 A1 * | 2/2003 | Matsuoka | A63B 21/0004 | 482/124 |
| 2003/0130098 A1 * | 7/2003 | Marco | A63B 21/0004 | 482/124 |
| 2005/0227833 A1 * | 10/2005 | Wilkinson | A63B 21/0004 | 482/124 |
| 2005/0251895 A1 * | 11/2005 | Farrah | A41D 1/08 | 2/227 |
| 2005/0261113 A1 * | 11/2005 | Wilkinson | A63B 21/0004 | 482/124 |
| 2007/0213186 A1 * | 9/2007 | Longo | A63B 21/0552 | 482/121 |
| 2008/0103032 A1 * | 5/2008 | Jacob | A63B 23/03575 | 482/124 |
| 2008/0182735 A1 * | 7/2008 | Thomas | A63B 21/4005 | 482/139 |
| 2010/0204014 A1 * | 8/2010 | Hoffman | A63B 21/055 | 482/8 |
| 2010/0274284 A1 * | 10/2010 | Cosgrove | A61H 1/0292 | 606/237 |
| 2011/0247127 A1 * | 10/2011 | Pou | A41D 13/0012 | 2/227 |
| 2013/0131724 A1 * | 5/2013 | Harada | A61H 1/008 | 606/237 |
| 2014/0005015 A1 * | 1/2014 | Hester | A63B 21/154 | 482/131 |
| 2014/0081185 A1 * | 3/2014 | Azevedo | A63B 69/0059 | 601/23 |
| 2016/0193517 A1 * | 7/2016 | Angulo | A63B 69/0057 | 482/92 |

* cited by examiner

BODY ALIGNMENT AND CORRECTION DEVICE

CROSS-REFERENCE TO RELATED APPLICATIONS

This application is a continuation of patent application Ser. No. 15/075,072, filed Mar. 18, 2016, which is a continuation-in-part of patent application Ser. No. 14/987,148, filed Jan. 4, 2016, which claims the benefit of Provisional Patent Application No. 62/099,606, filed Jan. 5, 2015, which applications are hereby incorporated by reference in their entireties.

FIELD OF THE INVENTION

The invention relates generally to exercise equipment and in particular to a body alignment and correction device.

BACKGROUND OF THE INVENTION

Exercise equipment, particularly when used in an athletic club, has become very popular. Unfortunately, to put it simply, most people who are working out are doing it less effectively or wrong. They hold their bodies—their core and limbs—in incorrect positions, whereby their core is not properly engaged, which results in repetitive motion injuries, imbalanced development of their muscle groups, and other long-term problems that are easily avoided with the correct posture and limb positioning. A body alignment and correction device, which secures the user's core and limbs in the correct positions when working out, would resolve this problem.

SUMMARY OF THE INVENTION

A body alignment and correction device for use by a human user includes a belt for wearing about the user's waist and having a front and a back, an outer surface facing away from the user's body, an inner surface facing toward the user's body, and fastening means at the front for fastening said belt around the user's body; and includes a shoulder system having a shoulder strap, connection means for connecting the belt to the shoulder strap and to a pull cord fixable to an external object, the shoulder being strap configured to extend around the user's shoulders Additional features and advantages of the invention will be set forth in the description that follows, and will be apparent from the description, or may be learned by practice of the invention. The foregoing general description and the following detailed description are exemplary and explanatory and are intended to provide further explanation of the invention.

BRIEF DESCRIPTION OF THE DRAWINGS

The accompanying drawings are included to provide a further understanding of the invention and are incorporated into and constitute a part of the specification. They illustrate one embodiment of the invention and, together with the description, serve to explain the principles of the invention.

DESCRIPTION OF THE PREFERRED EMBODIMENT

For the purposes of promoting an understanding of the principles of the invention, reference will now be made to the embodiments illustrated in the drawings and specific language will be used to describe the same. It will nevertheless be understood that no limitation of the scope of the invention is thereby intended, and any alterations or modifications in the illustrated device, and any further applications of the principles of the invention as illustrated therein are contemplated as would normally occur to one skilled in the art to which the invention.

Figure 1:
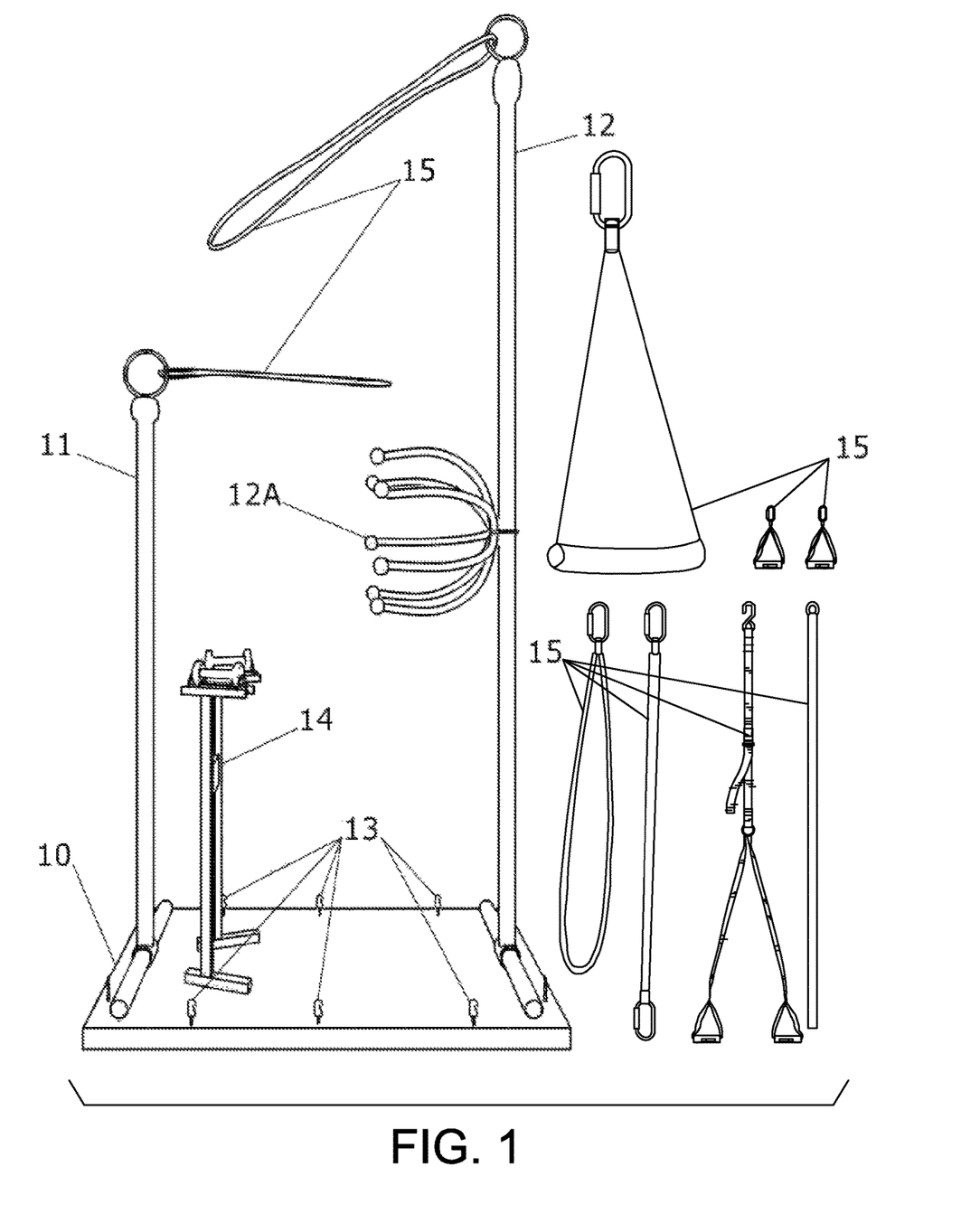
FIG. 1 is a side perspective view of a body alignment and correction device 5 in accordance with one embodiment of the present invention, shown in the unfolded position, displaying the platform 10, the front post 11, the rear post 12, the claw attachment 12A, the carabiner clips 13, the barbell table 14, and the workout attachments 15.

Referring to the figures, and particularly to FIG. 1, there is shown a body alignment and correction device 5 in accordance with one embodiment of the present invention and which is primarily designed for use during workouts. Device 5 provides a rectangular platform 10, with a front post 11 and a rear post 12, which unfold and telescope into position, rotate fully through a 180° arc, and may be locked into position at any length or angle as desired. Carabiner clips 13 are provided along the sides of the platform 10. Various elastic and other workout attachments 15 may be clipped to the carabiner clips 13, and to the upper ends of the front post 11 and rear post 12, providing resistance for the user during a workout.

An adjustable, removable claw attachment 12A on the rear post 12 can hold an exercise ball for certain exercises. A removable barbell table 14 may be secured to the platform 10, enabling the user to work out with barbells or other hand weights while secured in the correct posture by the claw attachment 12A. Four retractable caster wheels 10A (FIG. 2) at the corners of the platform 10 enable the user to easily move the device around the workout area as desired. The platform 10 is hinged in the center such that it may be folded in half for easy transport and storage.

Referring to FIGS. 3-7, device 5 may further include a broad, padded belt 16 with hook-and-loop fasteners 21 at each of its opposing ends. The belt 16 is preferably 3-4 inches wide. The layers of the belt 16 are affixed to each other with snaps 17 to form a sleeve. The layers of the belt 16 may also be fastened with other fastening devices such as zippers and hook and loop fasteners. The layers of the belt 16 may also be sewn together with stitching. Flat bands 19, terminating in rings or carabiner style belt clips 18, are provided to extend through the sleeve of the belt 16, which may be used as drawstrings to tighten and secure the belt 16 around the user's waist to secure the belt 16 to the user's body.

Figure 6:
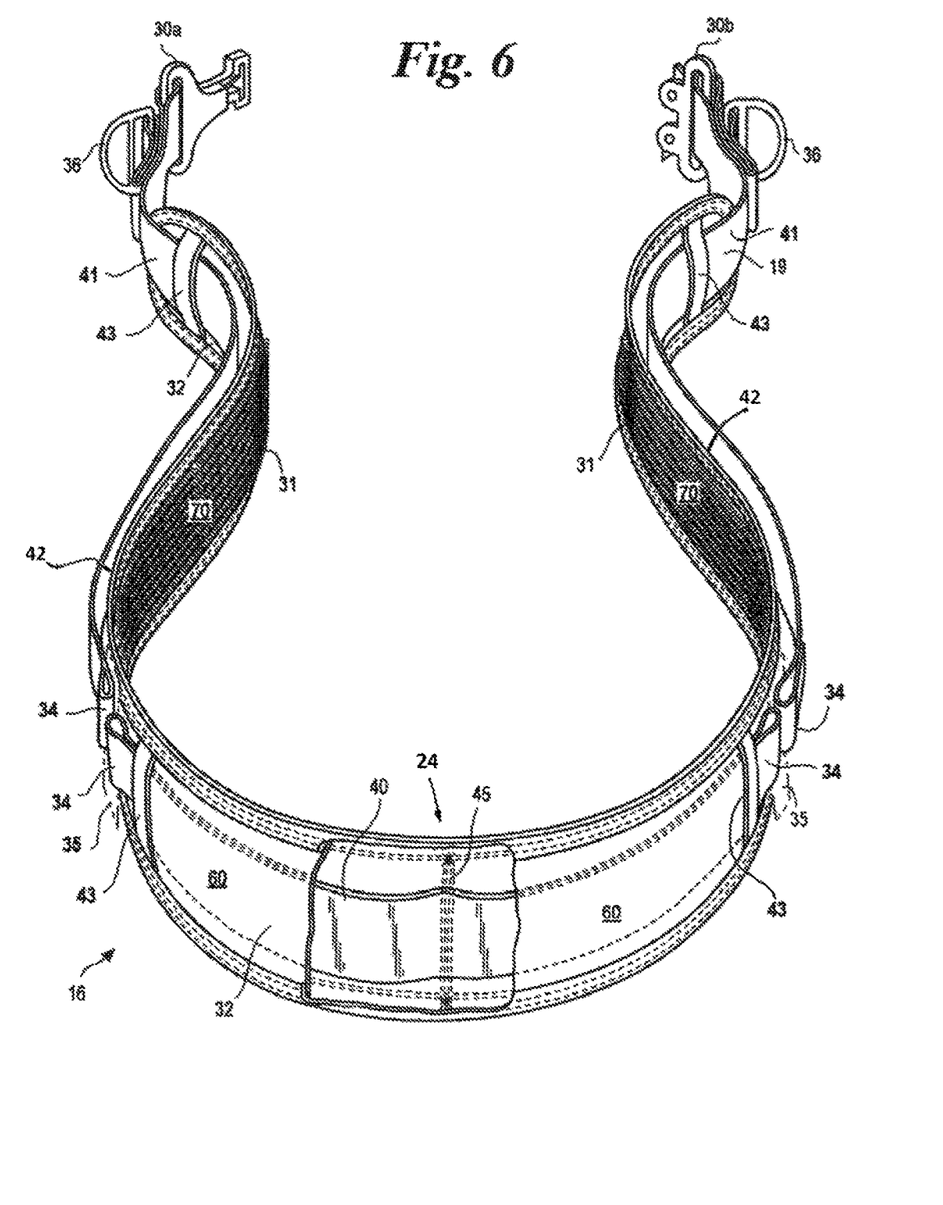
FIG. 6 is a perspective view of an embodiment of the belt 16 of the invention, without blocks.
Figure 7:
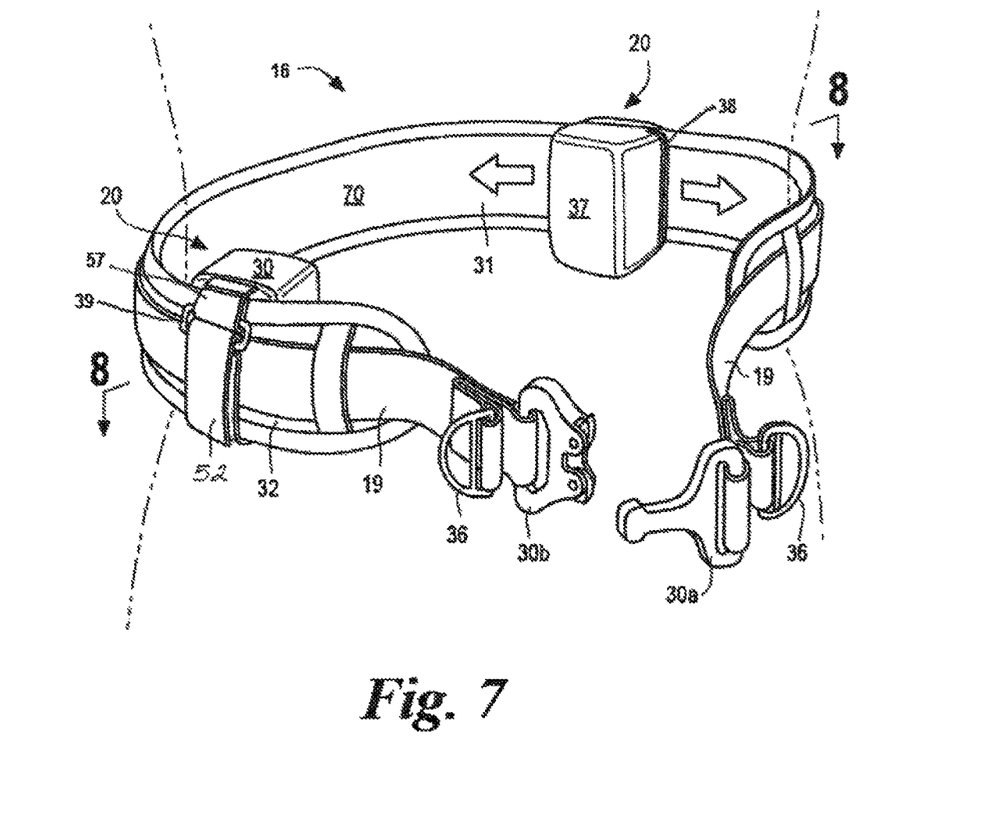
FIG. 7 is a perspective view of an embodiment of the belt 16 of FIG. 6 with a pair of blocks 20 positioned on the inside surface of the belt, one block 20 shown positioned at the back of the belt for engagement at the outside of the user's back and the other block 20 shown at the front of the belt for engagement at the outside of the user's abdomen.

In other embodiments, the bands 19 may each terminate in a complementary buckle member 30a and 30b, as shown in FIGS. 6 and 7, so that the bands 19 may be fastened in front of the user when worn. Thus, when the buckle members 30a and 30b are connected to each other, they are at the front of the belt 16, and the opposing side of the oval, connected belt 16 is the back or rear 24 of the belt 16 (see FIGS. 8a and 8b). The bands 19 may also include adjustment buckles 35 so that the bands 19 may be adjusted in length. In other embodiments, the buckles 35 may be used to join or connect portions of the bands that have different characteristics, such as elasticity. A D-ring 36 is attached to the front ends of each band 19, near the buckle members 30a and 30b. The bands 19 are preferably 1.5 inches wide, and covered for two-thirds of their length with neoprene sleeves. Rivets and snaps 17 hold the neoprene sleeves together. However, in some embodiments, the bands need not be covered.

The snaps 17 enable the user to remove and replace the bands 19 if they are broken or worn out, or if the belt 16 needs to be laundered. Belt 16 further includes foam blocks 20 for distancing a portion of the belt 16 away from a specific portion of the wearer's body. Foam blocks 20 may be positioned such that they are just above the kidneys on the back 33 (FIG. 8b) for users who are flexion intolerant. This allows the belt 16 to only contact the user's abdomen, not the lower back. Alternatively, the foam blocks 20 may be positioned such that they are just above the hip bones in front (FIG. 8a) for users who are extension intolerant. This allows the belt 16 to only contact the user's lower back, not the abdomen.

In other embodiments, as shown in FIG. 6, the bands 19 may include an elastic portion 40, inelastic portions 41 and a base member 42. Base member 42 is a flexible strap sized to nearly encircle the waste of the user and includes guide straps 43, which are spaced apart along the outside of base member 42. The guide straps 43 each form a tunnel with base member 42 through which the elastic and inelastic portions 40 and 41 extend and are held in their desired positions along base member 42. The elastic portion 40 is preferably attached to belt 16 at the midpoint of its length. The elastic portion 40 may be secured to belt 16 by any means known. As shown in FIG. 6, the elastic portion 40 is secured to the midpoint of belt 16 by stitching 45. While the entire band 19 may be made of elastic, in the most preferred embodiment the elastic portion 40 is attached, at its opposing ends, to the inelastic portions 41. Inelastic portions 41 and elastic portion 40, together, are sized to surround the user and here form the elastic bands 19 (here the elastic and inelastic portions 40 and 41 can be considered to form, together, a single band 19 or two bands connected at 45 at the back 24. Thus, band 19 and bands 19 may be used interchangeably herein to refer to the unit or units that are connected to and/or held by base member 42, terminate at opposing ends in buckle members 30a and 30b (or similar fastening elements), and exhibit elasticity at their opposing ends at buckle members 30a and 30b. The elastic and inelastic portions may be attached to one another (at 35) by stitching, snaps, buckles, or any other mechanism known to attach bands. As shown in FIG. 6, each band portion includes a loop 34, which is fitted through (connected to) a buckle (represented at 35). In the most preferred embodiment, buckles 35 are adjustment buckles, which allow the user to adjust the overall length of the bands 19. In other embodiments, the length of the bands 19 may be adjusted at the buckles 30a and 30b. In other embodiments, buckles 35 may be omitted and the portions of the bands may be joined to each other with stitching.

As shown in FIG. 6, belt 16 may include an additional piece of material 60 along a portion of its length to partially conceal some portion of the bands 19. In the embodiment shown in FIG. 6, the additional piece of material 60 is approximately ¼ of the length of the belt 16, and is located at about the midpoint of the belt's length. Such location is generally to the rear of the user when the belt is worn by a flexion intolerant person, for example, (with the belt buckled in the front 34, FIG. 8b). Additional piece of material 60 is fastened to the outer surface 32 of the base member 42 so as to form a tunnel in which a portion of the band 19, may run or reside. The outer surface 32 of the belt 16 (and of base member 42) is the surface that is away from the user when the belt is worn. Specifically as shown in FIG. 6, the elastic portions 40 of bands 19 are partially covered by the additional piece of material 60. In the preferred embodiment shown in FIG. 6, the upper and lower perimeter edges of material 60 are sewn or otherwise fastened to the outer surface 32 of base member 42. In other embodiments, additional piece of material 60 may be omitted and the tunnel created between the outer surface 32 and the inner surface 31 of base member 42. In other words, base member 42 comprises a sleeve, at least along a portion or portions of its length, formed between inner and outer surfaces 31 and 32, respectively, or between outer surface 32 and straps 43 and material 60. In the latter case then, the bands 19 are positioned for part of their length, through the sleeves and against the outer surface 32.

Figure 8A:
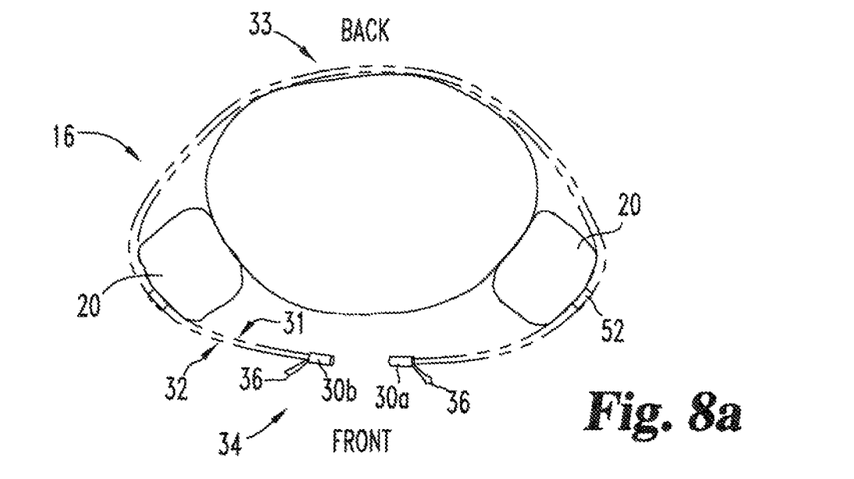
FIG. 8a is a representational, top, and cross-sectional view of the belt 16 of FIG. 7, taken along the lines 8-8, viewed in the direction of the arrows, and with blocks 20 positioned proximal the abdomen for use by an extension intolerant user.
Figure 8B:
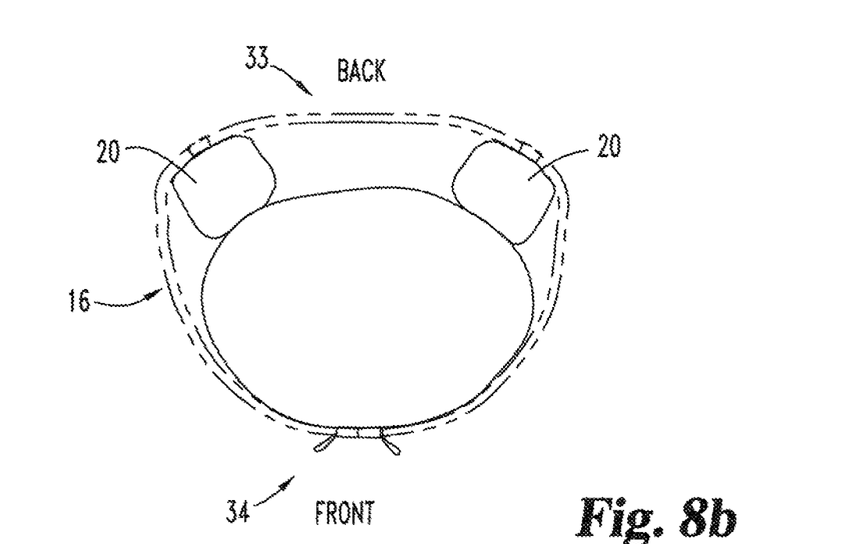
FIG. 8b is a representational, top, and cross-sectional view of the belt 16 of FIG. 7, taken along the lines 8-8, viewed in the direction of the arrows, and with blocks 20 positioned proximal the user's back for use by a flexion intolerant user.

Foam blocks 20 are affixed to some appropriate portion of belt 16, such as the base member 42, such that when the belt 16 is worn by a flexion intolerant person (or "flexion" for short) (as described herein), the foam blocks 20 are located on or below the user's kidney area. Thus, to achieve a placement generally in line below the kidneys at the user's back 33 (FIG. 8b) or above the hip bones at the user's front 34 for an extension intolerant person (an "extension", for short) (FIG. 8a), the blocks 20 are spaced about 120 degrees apart from each other, on a belt connected to itself (buckle 30a to buckle 30b) to surround and thus be supported by a person. This approximation (120 degrees) permits slight adjustment to find the preferred comfortable position by the user, and it means that the blocks 20 are positioned not right next to each other, and not 180 degrees apart. The purpose, as stated herein, is that the blocks 20 are positioned, spaced apart (about 120 degrees) on the belt 16 (on the base member 42 or otherwise connected to belt 16) so that the belt 16 extends in contact across the (flexion) user's abdomen, but is spaced away from the (opposing) user's lower back (FIG. 8b); or, conversely, for an extension intolerant person (an "extension"), the blocks 20 are positioned so that belt 16 extends in contact across the user's lower back, but is spaced away from the user's (opposing) abdomen (FIG. 8a). In the preferred embodiment, the dimensions of the foam blocks 20 are approximately 2.5" (thickness)×3" (width)×4.5" (length). Foam blocks 20 are preferably made of at least two types of foam to provide a firmer base of support nearer the belt 16. In the most preferred embodiment, foam blocks 20 are constructed of a first layer of high density foam 22, and a second layer of lower density foam 23. The high-density foam 22 is preferably 0.5 inches thick, and the lower density foam 23 is approximately 2 inches thick. The high-density foam is positioned nearer that portion of the block that is to be connected to and at the inner surface 31 of belt 16, which helps the foam block 20 maintain its shape and resist rolling or deformation about the belt 16 during use.

Foam blocks 20 are removable in the event that the user wishes to rely on the pull of the bands 19. The inner surface 31 of belt 16 (of base member 42), which is the surface that faces the user when belt 16 is worn, may include hook and loop fastener material 70 on a portion of its length to allow the foam blocks 20, or enclosures or coverings 37 for the foam blocks, to be selectively attached at various positions along the belt 16. In such embodiment, the surface of the foam block 20 or its enclosure or covering 37 has a hook and loop fastener material 70 on its outer surface that is complementary to the hook a loop fastener material on the inner surface 31 of base member 42. In some embodiments, the inner surface 31 of base member 42 will include hook and loop fastener material 70 on substantially its entire length. The presence of the hook and loop fastener material 70 on substantially the entire length of the base member 42 allows foam blocks 20 (or their enclosures 37), which have complementary hook and loop fastener material 70 placed on their exteriors, to be positioned anywhere on the inner surface 31 of base member 42. With such positioning options, the user may easily move the foam blocks 20 to contact the user's back (kidney area) or abdomen (front hip bone areas), as desired.

Figure 9:
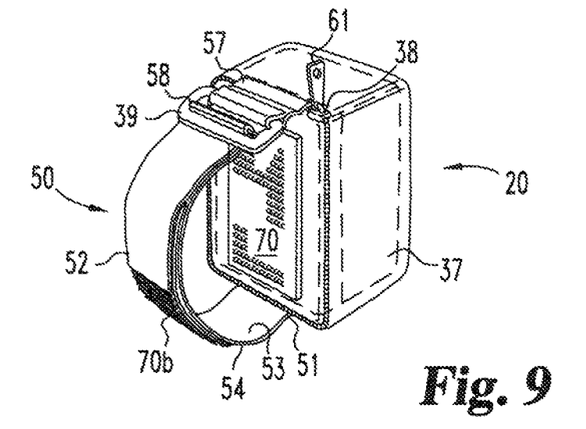
FIG. 9 is a perspective view of a block 20 of the device 5 of FIG. 7 and with an enclosure and attachment assembly 37/50.
Figure 10:
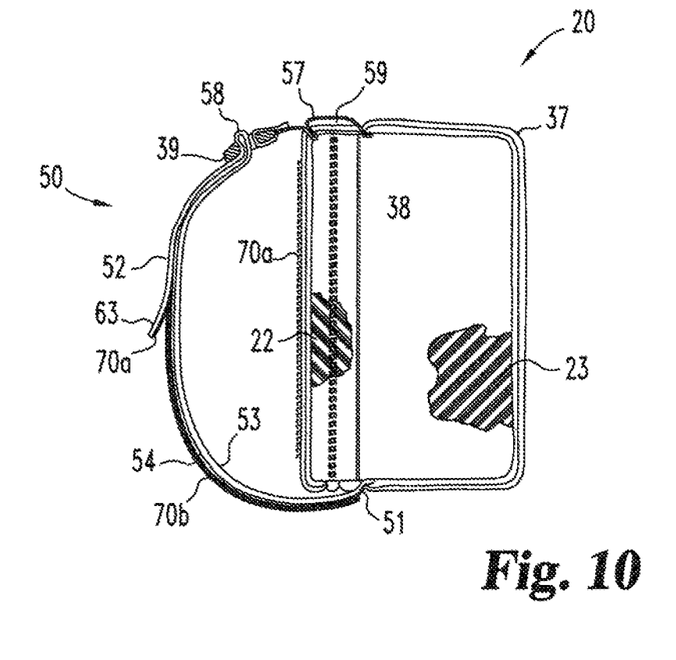
FIG. 10 is a side elevation view of the block 20 of FIG. 9, with breakouts showing composition of the block.

Preferably, foam blocks 20 are placed in an enclosure or covering 37, as shown in FIGS. 9 and 10. This prevents deterioration of foam blocks 20 from abrasion or from contact with the user's perspiration. The enclosure or covering 37 preferably covers all sides of the blocks 20 and includes a closing device such as a zipper 38 to allow a block to be inserted and removed. This is of benefit if the enclosure or covering 37 becomes damaged or soiled and needs to be repaired or laundered. As shown in FIGS. 9 and 10, the zipper 38 is preferably placed about the perimeter (along an edge) of a surface of the enclosure 37. Zipper 38 is proximal the surface of the enclosure that attaches or abuts the inelastic portion 41 of belt 16 when the block is placed on base member 42. Zipper 38 ends adjacent to a block securing assembly that is used to attach and further secure the enclosure or covering 37 to the belt. In such arrangement, when the zipper is closed, the zipper pull or tab 61 is placed underneath a portion of the securing assembly so that zipper pull 61 is restrained and does not move about as the user exercises.

The enclosure or covering 37 preferably also includes hook or loop fastener material 70 on at least one outer surface so that it can be attached to selected locations along the inner surface of base member 42. In the preferred embodiment, the loop portion of the fasteners are located on the inner surface 31 of base member 42, and the complementary hook portions are on the block enclosure or covering 37.

The enclosure or covering 37 may also include a block securing assembly 50 to further secure the blocks 20 to the belt 16. The block securing assembly 50 generally connects to the top and bottom of a block enclosure or covering 37, and is positioned so that the belt 16 is captured between a strap 52 of the assembly 50 and a block 20 and its enclosure or covering 37. Strap 52 is a length of webbing approximately 2 inches wide and 7 inches in length. Block securing assembly 50 further includes a slotted loop or buckle 39 attached directly, or by a web 57, to the top of the enclosure or covering 37. An upper end 58 of strap 52 is connected to buckle 39 and a lower, opposing end 51 of strap 52 is attached to the bottom of the enclosure or covering 37, as shown. In the embodiment shown in FIGS. 9 and 10, web 57 is attached to the top surface of the enclosure 37 with two lines of stitching so as to form a tunnel 59 into which the zipper pull 61 can be placed when zipper 38 is closed. Web 57 may be made of an elastic material, which allows tunnel 59 to be easily stretched and lifted by the user, allowing the zipper pull 61 to be inserted into tunnel 59 and held secure. With the enclosure or covering 37 positioned on the inner surface 31 of base member 42, strap 52 is positioned so that it extends over and against the outer surface 32 of base member 42, and the free end 63 of strap 52 is fed through slotted loop 39. Free end 63 of strap 52 is then pulled tight and secured against itself with fasteners, such as snaps or complementary hook and loop fastener material 70, as shown in FIGS. 7, 9, and 10.

In this embodiment, strap 52 has an inner surface 53 and an outer surface 54. On a first portion of the outer surface 54, near the free end 63, is attached the hook portion 70a of the hook and loop fastener material 70, and on a second portion of the outer surface 54, from the connection at 51 to the bottom of the enclosure or covering 37, is attached the loop portion 70b of the hook and loop fastener material 70. In the preferred embodiment, the hook and loop portions 70a and 70b each occupy about ½ of the length of the outer surface 54 of strap 52. With this arrangement, when strap 52 is pulled tight, the free end 63 of strap 52 is pulled through the slotted loop 39, and strap 52 is then folded about the slotted loop 39 and down against itself so that hook portion 70a of free end 63 engages with and against loop fasteners 70b on the lower portion of the strap 52. The free end 63 of strap 52 is thereby positioned at or near the lower end of the enclosure or covering 37. In the preferred embodiment, free end 63 extends no more than a half inch below the lower end of the enclosure 37. One skilled in the art will recognize that the hook portions 70a and loop portions 70b may be substituted for one another. However, one skilled in the art will also realize that it is preferable to have the loop fasteners 70b positioned in areas that will be exposed to the user or the user's clothing, as the hook fasteners 70a can be rough and abrasive. This observation holds true not just for the coverings or enclosures 37, but also for the positioning of the hook and loop fastener materials 70 on the belt 16.

In use, the user may place the platform 10 in the workout area, extend the front pole 11 and the rear pole 12 at any angle and to any length desired, and lock them into position. The user may then attach one or more workout attachments 15 to the carabiner clips 13, or the upper ends of the front pole 11 and the rear pole 12, as desired. The user may secure the claw attachment 12A to the rear pole 12 at the desired height and secure a stability ball therein for the workout. Alternately, the user may secure the barbell table 14 to the platform 10 and work out with barbells or other hand weights. The user may also wear the belt 16 around the waist and secure a cable or cord to and between belt 16 and poles 11 or 12, depending on whether the user is a flexion or an extension.

Figure 2:
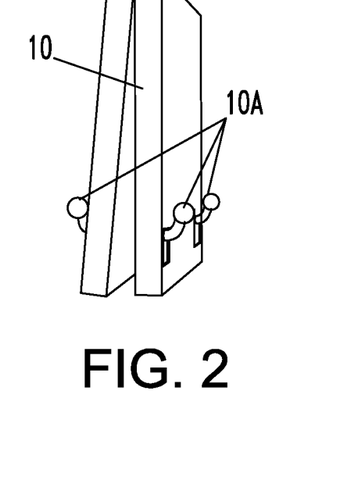
FIG. 2 is a side perspective view of the platform component 10 of the body alignment and correction device 5 of FIG. 1 shown in the folded position, displaying the platform 10, and the caster wheels 10A.
Figures 3, 4:
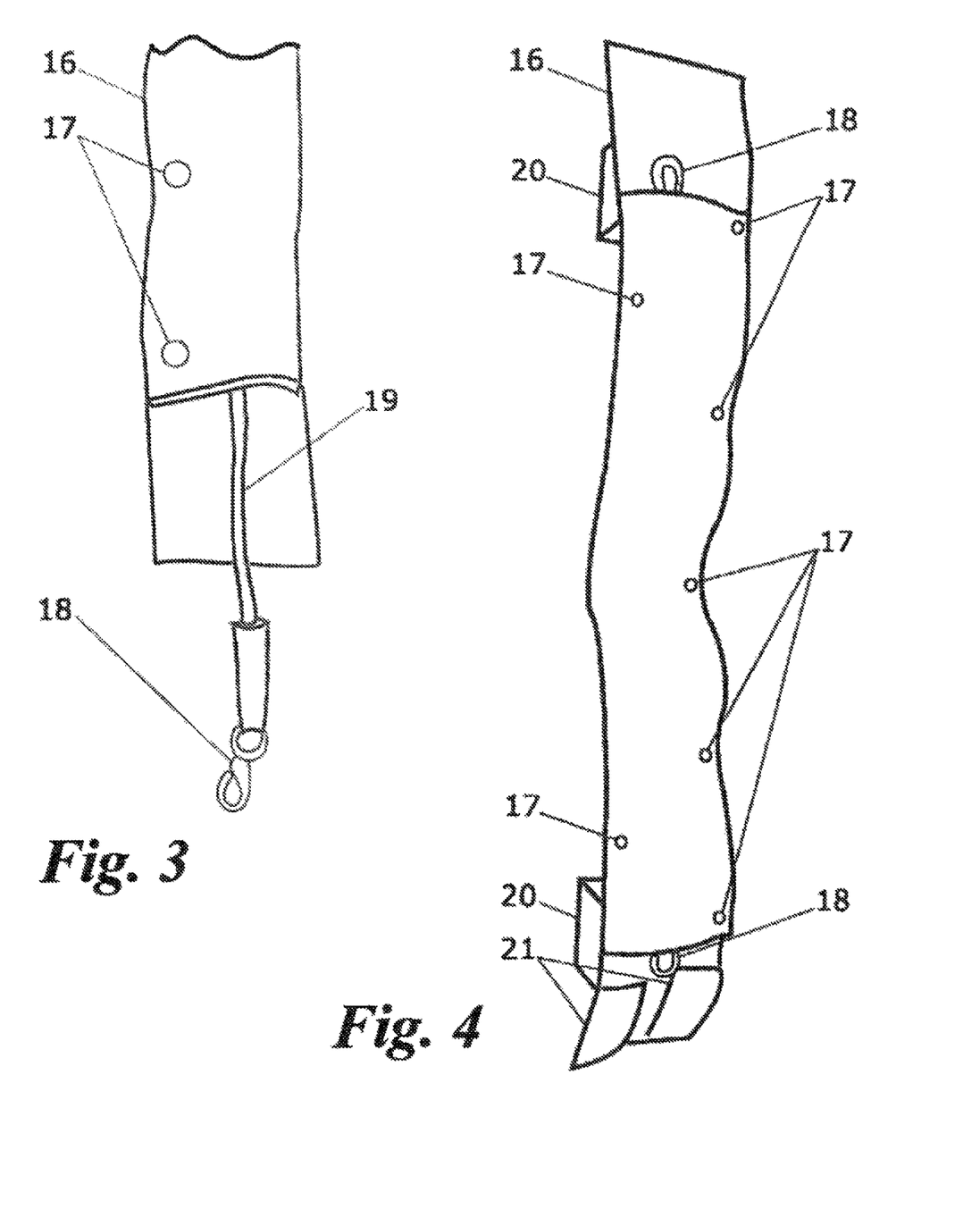
FIG. 3 is a rear view of a portion of the belt 16 of the body alignment and correction device 5 of FIG. 1.
FIG. 4 is a rear view of the belt 16 of FIG. 3.
Figure 5:
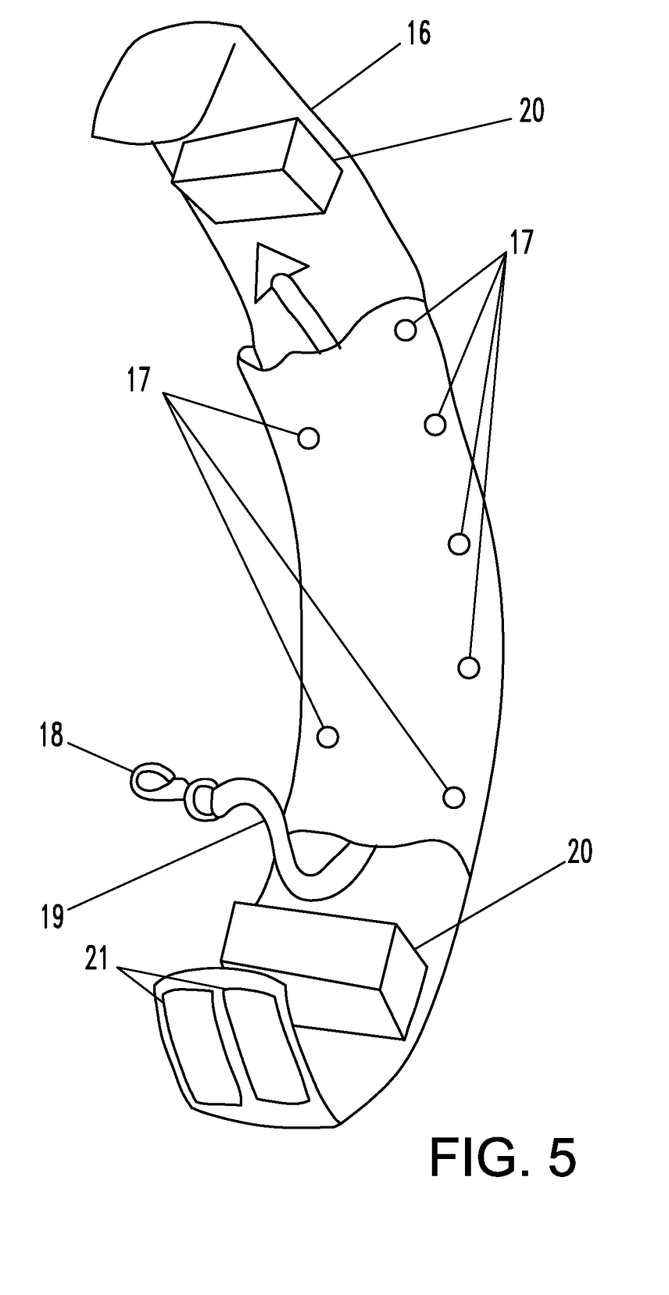
FIG. 5 is a front view of the belt 16 of FIG. 3 shown in a reverse bent position.

When finished with the workout, the user may extend the caster wheels 10A and roll the platform 10 wherever desired. Alternately, the user may detach the barbell table 14 or the workout attachments 15 and remove the claw attachment 12A. Then the user may unlock, retract, and fold the front post 11 and the rear post 12, and fold up the platform 10 for transport or storage.

Device 5 is a flexion extension dominant system, which determines the environment wherein a particular human body will function at its highest level. This flexion extension dominant theory was derived from the rehabilitation concepts of flexion intolerance and extension intolerance. Flexion intolerance is posterior chain weakness, while extension intolerance is anterior chain weakness. When the intolerance (anterior or posterior dominance and/or weakness) is observed, the therapist can determine the injury trail a patient may have and lifestyle influences, such as employment and sports in which the patient would excel. This information could substantially impact future wear and tear on joints, direction of an athlete in particular sports, and which employment career is best suited for an individual. It is also observed that this may have an influence on the learning styles of various people based on environments.

It is found that flexion intolerant people ("flexions") have possible damage to the spine where it is advised for them not to crunch or flex the spine forward. However, they need to keep their core, abdominal muscles and posterior chain stimulated by application of a force pulling from their back or rear side, such as a backpack or a band, and/or by application of pressure against the lower abdominal muscles. If not stimulated, their posterior muscles will not activate fully, which can lead to compensatory patterns—that is, other muscles are used (instead of the proper use of the posterior (chain) muscles), which leads to muscular imbalance, joint dysfunction and injury. These people tend to prefer standing more than sitting, and they tend to lean on objects such as tables and counters for relief. These people like to sleep on the side or the stomach. They tend to have weak hamstrings, biceps, shoulders, upper trapezius, upper chest, lower back, and calves. The common overuse injuries are ACL tears, arthritic hips, ab tears, calf tears, bicipital tendinitis, low back injuries like herniations, lordosis, and neck issues. Diastasis is also noted. These people tend to prefer activities where they push down, lift a knee, or use their abdominal muscles, such as mopping floors, massaging, hiking uphill, and picking up items from the floor or lower shelves. Sports these people excel in are sprinting, hockey, wrestling, kickboxing, and soccer. Careers these people excel in are massage therapy, construction, flooring installation, dentistry, architecture and cleaning. These people tend to comprehend best while looking down or writing, such as highlighting a book or using an iPad. For flexion intolerant people ("flexions"), belt 16 of device 5 is worn with its blocks 20 positioned at the outsides of the rear and where it (belt 16) touches the abdominal muscles and not the lower back; or a band can be worn touching the abdominal muscles and pulling the hips backward where a flexion intolerant person will then better or properly engage the posterior chain. This pull against the abdominal muscles allows the shoulders and hamstrings to properly activate and develop. Belt 16, the device, and the cardio attachments help apply this force to the abdomen to produce proper body mechanics that traditional exercises are missing.

It is found that extension intolerant people ("extensions") have possible damage to the spine where it is advised for them not to hyperextend the spine or dead lift. However, they need to keep their lower back or extensor muscles stimulated by application of a force pulling from their front side, such as a front pack below the neck, or by a band, or pressure against the lower back. If not stimulated, their anterior muscles will not activate fully, which can lead to compensatory patterns—that is, other muscles are used (instead of the proper use of the anterior (chain) muscles), which leads to muscular imbalance, joint dysfunction and injury. These people tend to like to sit and sleep on their sides or their backs. They tend to have weak quadriceps, latissimus dorsi, lower chest, abdominals, gluteus, and triceps. The common overuse injuries are Achilles tendinitis, Achilles rupture, meniscus tears, quadriceps tears, hip pain, slipped discs, torn rotator cuffs, cervical problems, kyphosis, tennis elbow, and carpal tunnel. Hernias are also noted. These people tend to like activities where they stand tall, extend their arms above the head, sit up straight, and hold weight in front of them. Sports these people tend to excel in are gymnastics, basketball, baseball, golf, distance running, tennis, and dance. Careers these people excel in are hairdressing, computer programming/maintenance, food service, driving, and painting. These people tend to comprehend best while looking up or leaning back in a chair or bed. They tend to do better with desktop computers. Belt 16 is worn with its blocks 20 positioned at the outsides of the abdomen and where the belt thus touches the lower back and not the abdominal muscles, or a band can be worn touching the lower back and pulling the hips forward so that an extension intolerant person will then better or properly engage his anterior chain. This pull allows for the latissimus dorsi, abdominals, gluteus and quadriceps to properly activate and develop. Belt 16, alone or with other elements of the device 5, help apply this force to produce proper body mechanics that traditional exercises are missing.

Device 5, and particularly belt 16, improves health care, injury prevention and rehabilitation, lowering incidences of injury and speeding up rehabilitation. Work related injuries that will be reduced include headaches and those affecting the lower back, knees, carpal tunnel and neck. Device 5 will assist in directing people into sports and careers, including military specialties, that are compatible with their body type. Device 5 may help improve sexual enjoyment and fertility, indicating which positions may be most suitable. Device 5 will help with exercise and obesity control since people do not like to experience pain when working out—people are more likely to maintain and complete a regular workout regimen when the workout is pain free. Device 5 will help with sleep positions and the selection of vehicles, chairs, and other furniture to prevent discomfort, generally improving comfort and quality of life. Device 5 will also improve cognition and learning by informing the user regarding the best positions for reading.

Platform 10 and the barbell table 14 are preferably manufactured from a rigid, durable material, such as steel, aluminum alloy, or wood. The caster wheels 10A are preferably manufactured from a rigid, durable material such as steel or aluminum alloy, providing solid tires that are preferably manufactured from a flexible, durable material such as rubber or silicone. The front post 11, rear post 12, and carabiner clips 13 are preferably manufactured from a rigid, durable material such as steel or aluminum alloy. The claw attachment 12A is preferably manufactured from a rigid, durable material such as steel or aluminum alloy, and are coated with a flexible, durable material such as rubber or silicone.

The workout attachments 15 are preferably manufactured from a variety of rigid, durable materials such as steel, aluminum alloy, plastic and wood, and flexible, durable materials such as rubber and nylon webbing. Belt 16 is preferably manufactured from a flexible, durable material such as nylon webbing. The snaps 17 and belt clips 18 are preferably manufactured from a rigid, durable material such as plastic or steel. The bands 19 are preferably manufactured from a flexible, durable material with a substantial elastic quality, such as rubber, and are covered for two-thirds of their length by sleeves which are preferably manufactured from a flexible, durable material such as neoprene.

Foam blocks 20 are preferably manufactured from a semi-rigid, durable material such as foam rubber. Fasteners 21 are preferably manufactured from a flexible, durable material such as plastic or nylon. Components, component sizes, and materials listed above are preferable, but artisans will recognize that alternate components and materials could be selected without altering the scope of the invention. Further, those skilled in the art will recognize that when the application refers to foam blocks or block, the reference can refer to foam block alone, or foam blocks with an enclosure or covering or other assemblies to allow the blocks to be secured on the belt 16.

While the foregoing written description of the invention enables one of ordinary skill to make and use what is presently considered to be the best mode thereof, those or ordinary skill in the art will understand and appreciate the existence of variations, combinations, and equivalents of the specific embodiment, method, and examples herein. The invention should, therefore, not be limited by the above described embodiment, method, and examples, but by all embodiments and methods within the scope and spirit of the invention.

What is claimed is:

1. A body alignment and correction device for use by a human user having a body with kidneys and a waist, comprising:
    a belt for wearing about and being supported by the user's body, the belt having a first end, a second end, an outer surface, and an inner surface including one of hook and loop fasteners;
    fastening means for fastening the belt about the user's waist; and
    a pair of blocks consisting essentially of foam, movable on the belt and affixable to the inner surface of the belt such that when the belt is worn by the user, the blocks project inwardly toward and against the user and are and remain during use a fixed distance apart and located at the user's kidneys to space the device, between the blocks, away from contact with the user's body, each of said blocks having the other of hook and loop fasteners.

2. The body alignment and correction device of claim 1, wherein the blocks are enclosed in a fabric covering.

3. The body alignment and correction device of claim 2, wherein the fabric covering includes an attachment assembly including a strap to capture the belt between the fabric covering and the strap.

4. The body alignment and correction device of claim 1, wherein the belt includes a first band and a second band, each band attached to the outer surface of the belt, and each band having a free end terminating in a fastener.

5. The body alignment and correction device of claim 4, wherein each band is partially covered by a neoprene sleeve.

6. The body alignment and correction device of claim 4, wherein the first band and second band are usable as drawstrings to tighten the belt about the user's waist.

7. The body alignment and correction device of claim 4 wherein the first and second band have an elastic quality.

8. The body alignment and correction device of claim 4, further including an additional piece of fabric attached to the outer surface of the belt, the additional piece of fabric forming a tunnel, a portion of at least one of the first and second bands being positioned within the tunnel.

9. The body alignment and correction device of claim 4 wherein the first and second bands include an elastic portion and an inelastic portion, the inelastic portion being secured to the outer surface of the belt.

10. The body alignment and correction device of claim 1, wherein at least one of said blocks includes two densities of foam.

11. The body alignment and correction device of claim 10 wherein the blocks are enclosed in a covering, the covering including a hook and loop fastener on the surface of the covering facing the belt, a strap attached to a bottom end of the covering and a buckle attached to a top end of the covering, the strap being placed through the buckle and attached to itself to secure the belt between the strap and the covering.

12. The body alignment and correction device of claim 1 wherein at least one of the blocks includes hook and loop fasteners on a surface of the block.

13. A method for correcting body alignment of a human user having kidneys, hips, a waist, an abdomen, and a lower back, the method comprising the steps of:
    providing a body alignment and correction device including a belt for wearing about and being supported by the user's body and a pair of blocks consisting essentially of foam and movable on the belt, the belt having first and second ends and an inner surface, the device further including first fastening means for fastening the first and second ends together and second fastening means for affixing the pair of blocks to the inner surface;
    affixing the pair of blocks to the inner surface such that when the belt is worn around the waist by the user, the blocks are located at one of the user's kidneys and the user's hips; and
    positioning the belt around the user's waist and so that the blocks project inwardly toward and against the user and are and remain during use a fixed distance apart and located between the user and the inner surface and at one of a first position and a second position, the first position including the blocks located at the user's kidneys whereby the device contacts the user's abdomen but not the user's lower back between the belts, and the second position including the blocks located at the user's hips whereby the device contacts the user's lower back but not the user's abdomen between the blocks; and
    connecting the first and second ends together using the first fastening means.

14. The method for correcting body alignment of a human user of claim 13 wherein the providing step includes the second fastening means including the inner surface having one of hook and loop fasteners and each of the pair of blocks having the other hook and loop fasteners.

15. The method for correcting body alignment of a human user of claim 13, wherein the providing step includes the blocks being enclosed in a fabric covering that includes an attachment assembly including a strap to capture the belt between the fabric covering and the strap.

16. A body alignment and correction device for use by a human user having a body with kidneys and a waist, comprising:

a belt for wearing about and being supported by the user's body, the belt having a first end, a second end, an outer surface, and an inner surface;

first fastening means for fastening the belt about the user's waist;

a pair of blocks consisting essentially of foam, movable on the belt and affixable to the inner surface of the belt such that when the belt is worn by the user, the blocks project inwardly toward and against the user and are and remain during use a fixed distance apart and located at the user's kidneys to space the device between the blocks away from contact with the user's body; and second fastening means for affixing the blocks to the belt.

17. The body alignment and correction device of claim 16 wherein the second fastening means including the inner surface having one of hook and loop fasteners and each of the pair of blocks having the other hook and loop fasteners.

18. The body alignment and correction device of claim 16, wherein the blocks are enclosed in a fabric covering that includes an attachment assembly including a strap to capture the belt between the fabric covering and the strap.

\* \* \* \* \*